United States Patent [19]
Pudenz et al.

[11] Patent Number: 5,112,303
[45] Date of Patent: May 12, 1992

[54] TUMOR ACCESS DEVICE AND METHOD FOR DELIVERING MEDICATION INTO A BODY CAVITY

[75] Inventors: Robert H. Pudenz, South Pasadena; Gary P. East, Santa Barbara, both of Calif.

[73] Assignee: Pudenz-Schulte Medical Research Corporation, Goleta, Calif.

[21] Appl. No.: 694,679

[22] Filed: May 2, 1991

[51] Int. Cl.$^5$ .............................. A61M 29/00
[52] U.S. Cl. ........................ 604/49; 604/93; 604/97; 604/183; 604/891.1
[58] Field of Search .................. 604/8, 27-28, 604/48-49, 93, 96-97, 100, 131, 153, 173-175, 183, 891.1; 606/191-192; 128/DIG. 12

[56] References Cited

U.S. PATENT DOCUMENTS

| | | | |
|---|---|---|---|
| 4,312,353 | 1/1982 | Shahbabian | 606/192 |
| 4,543,088 | 9/1985 | Bootman et al. | 604/93 |
| 4,552,553 | 11/1985 | Schulte et al. | . |
| 4,588,394 | 5/1986 | Schulte et al. | . |
| 4,681,560 | 7/1987 | Schulte et al. | . |
| 4,681,564 | 7/1987 | Landreneau | 604/97 |
| 4,685,447 | 8/1987 | Iverson et al. | 604/96 X |
| 4,692,146 | 9/1987 | Hilger | 604/93 |
| 4,761,158 | 8/1988 | Schulte et al. | . |
| 4,778,452 | 10/1988 | Moden et al. | 604/93 |
| 4,802,885 | 2/1989 | Weeks et al. | 604/93 |
| 4,816,016 | 3/1989 | Schulte et al. | . |
| 4,840,190 | 6/1989 | Sasaki | 128/897 |
| 4,840,615 | 6/1990 | Hancock et al. | 604/93 |
| 4,929,236 | 5/1990 | Sampson | 604/175 |
| 5,087,244 | 2/1992 | Wolinsky et al. | 604/53 |

FOREIGN PATENT DOCUMENTS 716289 12/1931 France .................. 604/97

OTHER PUBLICATIONS

Advertisement for Intratumor Cyst Implant (one page).

*Primary Examiner*—C. Fred Rosenbaum
*Assistant Examiner*—C. Maglione
*Attorney, Agent, or Firm*—Kelly, Bauersfeld & Lowry

[57] ABSTRACT

A method for delivering a medication into a body cavity includes the steps of inflating a flexible bag within the body cavity such that the flexible bag expands to fill most of the void of the body cavity, and injecting medication into the space between an exterior surface of the flexible bag and the cavity wall such that the medication substantially surrounds the flexible bag and fills the remaining void. The steps of inflating the flexible bag and injecting medication are accomplished through subcutaneous injection at a site remote from the body cavity. To accomplish this, a surgically implantable tumor access device includes co-located first and second injection ports, for respectively, receiving a sterile fluid and a fluid medication. A flexible fluid conduit, which includes two coaxial tubes, directs the injected fluids, in a manner providing separate fluid flow paths, to a point adjacent to an inlet for the flexible bag. An inner tube fluidly connects the flexible bag with the first injection port. An outer tube surrounding the inner tube directs medication from the second injection port to medication delivery tubes fixed to an exterior surface of the flexible bag.

33 Claims, 2 Drawing Sheets

TUMOR ACCESS DEVICE AND METHOD FOR DELIVERING MEDICATION INTO A BODY CAVITY

BACKGROUND OF THE INVENTION

This invention relates generally to surgically implantable devices utilized to access selected portions of a body. More specifically, the present invention relates to implantable devices utilized to access a body cavity resulting from removal of a tumor or the like, which devices permit fluid access to the cavity at an injection site remote from a cavity wall aperture.

Many medical devices have been developed to provide access to selected body parts or systems. Some such devices are subcutaneously implantable and are controlled by percutaneous manipulation. Exemplary of such percutaneously manipulable devices are a broad family of cerebrospinal fluid shunts, one of which is illustrated in U.S. Pat. No. 4,552,553. Other subcutaneously implantable medical devices are utilized to direct medication to a particular portion of the body, wherein the medication is injected at a site remote from the delivery location. Exemplary of such devices are the subcutaneous infusion reservoir and pump systems found in U.S. Pat. Nos. 4,816,016; 4,761,158; 4,681,560 and 4,588,394.

In many infusion reservoir and pump systems, which may be utilized to direct a powerful pain killing drug such as morphine to the central nervous system on demand, a variable capacity reservoir is connected by tubing or the like to an injection port which receives medication by injection. The reservoir receives and stores fluid medication for delivery to a catheter which directs the medication to a specific infusion location in the body. Typically, a control assembly is interposed between the reservoir and the catheter to facilitate and control the transfer of the medication from the reservoir to the catheter in a safe and efficient manner. The control assembly is constructed to prevent the backflow of fluid from the catheter to the reservoir, as well as the unrestricted flow of medication through the control assembly.

In the treatment of cancer, physicians now have a wide variety of treatment methods which are useful in reducing the extent of the disease and, sometimes, in eradicating the disease from the patient. Such treatment methods include radiation therapy, chemotherapy, excision of the cancerous growth from the body, and often a combination of these alternatives. Intratumor cyst implants have been developed for the treatment of malignant gliomas of the nervous system in response to the need for reliable indices of tumor response to therapy, and access of sytotoxic agents to unresectable portions of the glioma. In such intratumor cyst implants, a prosthesis is implanted within the center of the glioma after surgical resection of a suitable core, or within the raw surfaces of the residual tumor if an extensive lobectomy is feasible. Samples of tumor extracellular fluid and tumor cells can be withdrawn at frequent intervals and medication injected repeatedly by the reservoir connected to the cyst implant. The reservoir provides an injection site remotely situated from the cyst implant. Prior intratumor cyst implant devices are not satisfactory, however, in many instances.

By way of example, after all or part of a cancerous growth has been excised from the body, it is often desirable to utilize chemotherapy medications or killer "T" cells to kill any remaining cancer cells lining the body cavity created by the excision. Prior intratumor cyst implants do not optimally lend themselves to such treatment since a cavity wall aperture must be quite large to permit the implant to be removed following treatment, or a second surgical procedure is required to remove the same from the cavity. Further, due to the inflexible nature of the implant, a large quantity of medication must be injected into the remote injection site for delivery, through a catheter or the like, to the cavity in order to fill a void defined by the cavity walls and ensure that adequate treatment is effected on the cavity walls.

Accordingly, there has been a need for a novel tumor access device which is completely subcutaneously implantable, of simple construction, and accessible through the skin of the patient by injection. Such a device should be insertable through a relatively small cavity wall aperture, be capable of substantially filling the void therein, and require a minimum quantity of medication for effective treatment of the tissue surrounding the cavity. Further, a tumor access device is needed which minimizes any surgical procedure required to remove the device from the body, and whose configuration within the patient is adjustable and can be detected through x-ray photography. Finally, there exists a significant need for a novel treatment method for accessing a body cavity through a relatively small cavity wall aperture, and for delivering medication into the body cavity. The present invention fulfills these needs and provides other related advantages.

SUMMARY OF THE INVENTION

The present invention resides in an improved tumor access device and a method for delivering medication into a body cavity. The novel method of the present invention comprises, generally, the steps of inflating a flexible bag within the body cavity utilizing a sterile fluid such that the flexible bag expands to fill most of the void of the body cavity, and injecting the medication into the space between an exterior surface of the flexible bag and the cavity wall such that the medication substantially surrounds the flexible bag and fills the remaining void. The steps of inflating the flexible bag and injecting medication are accomplished through subcutaneous injection at a site remote from the body cavity. In this manner many of the disadvantages associated with the prior art are eliminated, and in particular the amount of medication needed to effectively treat the walls of the body cavity is greatly diminished over prior treatment techniques.

To effect the method of the present invention, the tumor access device comprises, generally, a surgically implantable device for accessing the body cavity through a relatively small cavity wall aperture. The device includes a flexible bag which is configured for insertion into the body cavity through the cavity wall aperture, which bag has a bag inlet and a fluid impermeable exterior surface. Means are also provided for receiving by injection, at a location remote from the fluid impermeable bag, a fluid utilized for inflating the bag. A fluid conduit connects the fluid impermeable bag to the inflating fluid receiving means, such that fluid injected into the inflating fluid receiving means passes through the fluid conduit and the bag inlet to inflate the bag. Means are provided for receiving by injection, at a location remote from the fluid impermeable bag, medication into the device. Finally, means are provided for delivering the medication from the medication receiving means into a space between the walls of the body cavity and the exterior surface of the fluid impermeable bag.

In a preferred form of the invention, the fluid conduit extends between and connects the medication receiving means and the medication delivering means. Fluid injected into the medication receiving means passes through the fluid conduit into the medication delivering means for passage into the space between the walls of the body cavity and the exterior surface of the fluid impermeable bag. The fluid conduit includes a first section of tubing having a first end which receives fluid injected into the inflating fluid receiving means, and a second end which discharges fluid passing therethrough into the fluid impermeable bag through the bag inlet. The fluid conduit further includes a second section of tubing which is coaxial with and surrounds the first section of tubing for at least a portion of the length of the fluid conduit. The second section of tubing has a first end which receives fluid injected into the medication receiving means, and a second end which discharges fluid into the medication delivering means.

The fluid conduit is preferably constructed of barium impregnated silicone tubing to permit x-ray detection thereof when the device is subcutaneously implanted. Similarly, the fluid impermeable bag includes radiopaque markers which permit the configuration of the bag within the cavity to be determined by x-ray photography or the like.

The medication delivering means includes a plurality of medicinal tubes which are attached to and extend substantially equidistantly about a portion of the exterior surface of the fluid impermeable bag. Each medicinal tube has a first end in fluid communication with medication injected into the medication receiving means, and a second plugged end. Each medicinal tube further includes a plurality of apertures through which medication is delivered into the space between the walls of the cavity and the exterior surface of the fluid impermeable bag.

The inflating fluid receiving means includes a first injection port comprising a first base and a first self-sealing dome which define therebetween a fluid injection chamber. The first end of the first section of tubing is attached to the first injection port such that fluid injected into the fluid injection chamber freely passes therethrough for delivery to the fluid impermeable bag.

The medication receiving means includes a second injection port comprising a second base and a second self-sealing dome which define therebetween a medication injection chamber. The first end of the second section of tubing is attached to the second injection port such that fluid injected into the medication injection chamber freely passes through the second section of tubing for delivery to the medication delivering means.

In the illustrated embodiment, the first and second injection ports are co-located and share a common base. A needle guard is positioned within each of the injection chambers adjacent to the base, to prevent a needle inserted therein from passing through the base. This helps to ensure that the injected fluid is received by the device.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

Figure 1:
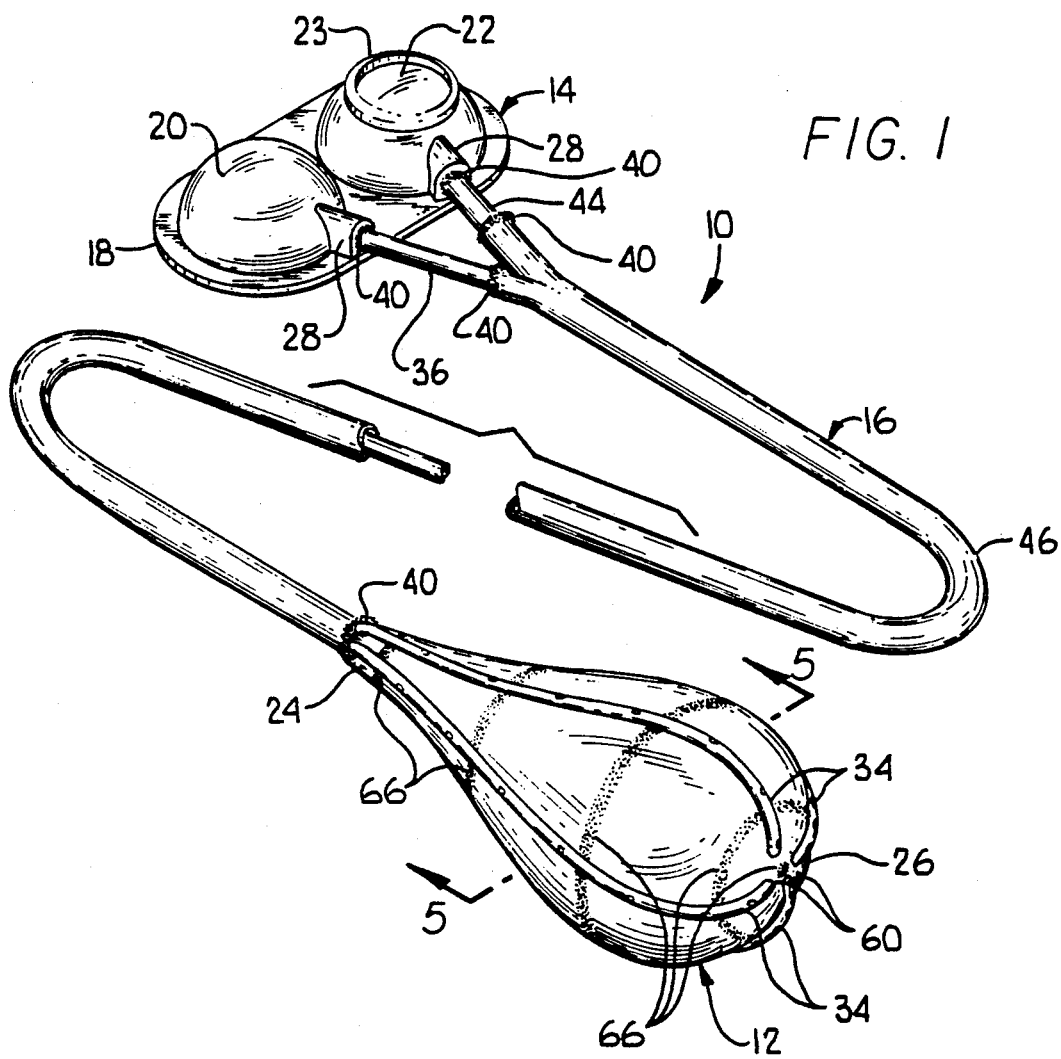
FIG. 1 is a perspective view of a tumor access device embodying the present invention, shown with a portion of a fluid conduit fragmented to show the configuration thereof.
Figure 2:
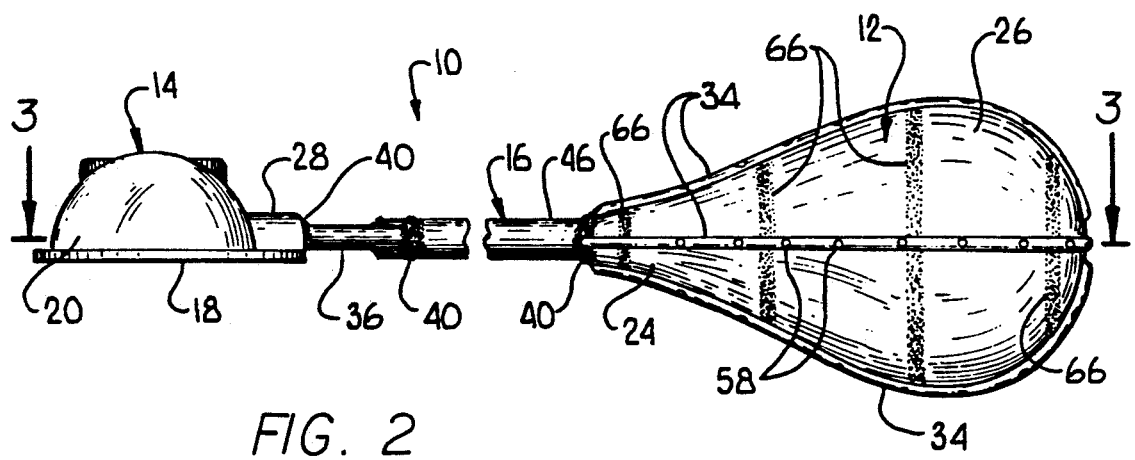
FIG. 2 is an elevational view of the tumor access device shown in FIG. 1.

As shown in the drawings for purposes of illustration, the present invention is concerned with a tumor access device, generally designated in the accompanying drawings by the reference number 10. The tumor access device 10 comprises, generally, a flexible bag 12 which is connected to an injection site 14 by means of a fluid conduit 16. The entire tumor access device 10 is designed to be subcutaneously implanted within the body of a patient such that the flexible bag 12 may be placed within a body cavity while the injection site 14 is situated at a location remote from a body cavity wall aperture.

Figure 3:
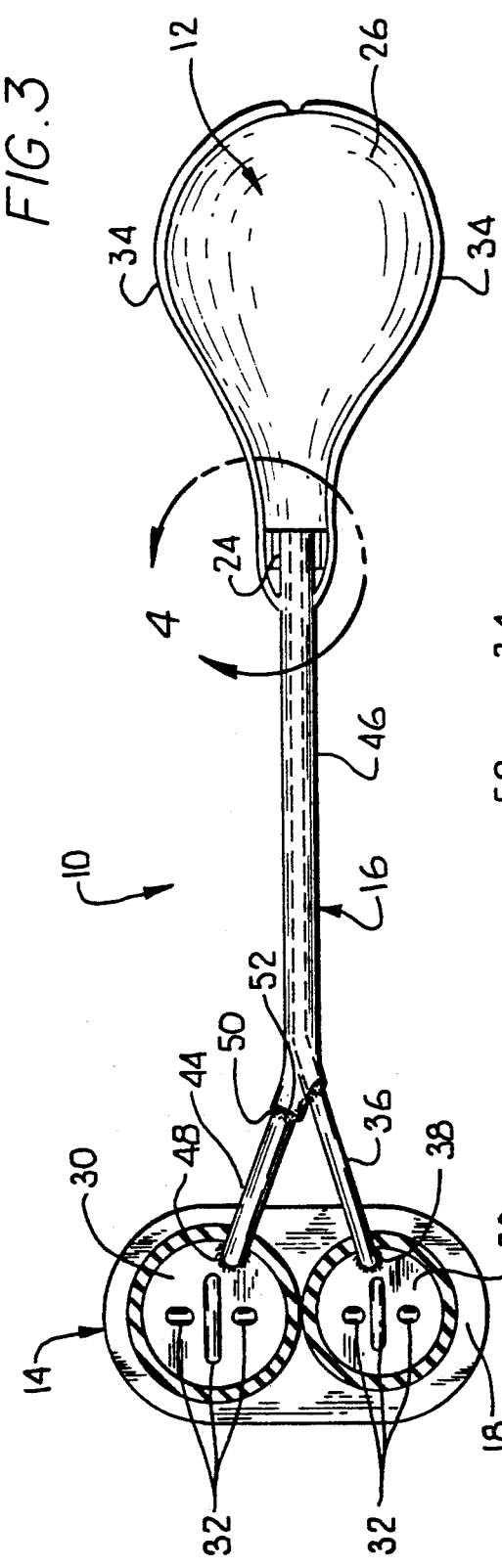
FIG. 3 is a sectional view of the device taken generally along the line 3—3 of FIG. 2, illustrating the manner in which two coaxial fluid conduits direct fluid from an injection site to an inlet of a fluid impermeable bag situated adjacent to a wall cavity aperture.

In accordance with the present invention, and as illustrated in FIGS. 1 through 5, the injection site 14 includes a base 18, and two self-sealing domes 20 and 22 which overlie the base 18 and define therebetween, respectively, a fluid injection chamber and a medication injection chamber. As illustrated in FIGS. 1 and 3, the first self-sealing dome 20 defines a first injection port and is connected to a portion of the fluid conduit 16 which communicates directly with an inlet 24 of the flexible bag 12, for purposes of inflating the bag 12 within the body cavity. The second self-sealing dome 22 defines a second injection port and is placed in fluid communication with a portion of the fluid conduit 16 designed to direct medication into the space between the walls of the body cavity and an exterior surface 26 of the flexible bag 12. The second self-sealing dome 22 includes an upwardly projecting ring 23 which facilitates percutaneous identification of the domes 20 and 22 when the device 10 is subcutaneously implanted.

Each of the self-sealing domes 20 and 22 are preferably constructed of a silicone elastomer material which permits repeated injection of fluids into the respective injection and medication chambers by small gauge needles when the injection site 14 is subcutaneously implanted. Further, each self-sealing dome includes an outlet 28 through which portions of the fluid conduit 16 extend. A needle guard 30 is positioned within each of the injection chambers adjacent to the base 18 of the injection site 14 in order to prevent a needle inserted through the self-sealing domes 20 and 22 from passing through the base 18. Each needle guard 30 includes raised sections 32 which help to ensure that, when the overlying self-sealing dome 20 or 22 is pressed downwardly upon the needle guard 30 or the base 18, the overlying dome will not adhere to the base, but rather reform to its original semispherical shape after the downward pressure is removed.

The fluid conduit 16 comprises several sections of surgical tubing which conduct fluids injected into the injection site 14 either to the bag inlet 24 or to a plurality of medicinal tubes 34 attached to the exterior surface 26 of the flexible bag 12 for directing fluid medication into a space between the exterior surface of the bag and the cavity walls. A first section of tubing 36 extends from the first self-sealing dome 20 to the bag inlet 24. A first open end 38 of the first section of tubing 36 is fixed within the outlet 28 provided through the first self-sealing dome 20 by means of a silicone adhesive 40. A second open end 42 of the first section of tubing 36 is secured within the bag inlet 24 in a manner which will be described in greater detail hereafter, such that fluid injected through the first self-sealing dome 20 is free to pass directly into the flexible bag 12.

A second section of surgical tubing 44 extends a short distance between the second self-sealing dome 22 and a third section of surgical tubing 46. A first open end 48 of the second section of surgical tubing 44 is inserted through the outlet 28 through the second self-sealing dome 22 and is secured in place by means of a silicone adhesive 40. A second open end 50 of the second section of surgical tubing 44 is enveloped by a first open end 52 of the third section of surgical tubing 46 and is secured in place by, once again, a silicone adhesive 40. The third section of surgical tubing 46 extends from the second open end 50 of the second section of surgical tubing 44 to a point within the bag inlet 24, where a terminal end 54 of the third section of tubing 46 is plugged in a manner to be hereafter described.

The first section of tubing 36 extends through an aperture provided in the third section of tubing 46 adjacent to its first open end 52, such that the third section of tubing is coaxial with and surrounds the first section of tubing for at least a portion of the length of the fluid conduit 16. The entry point of the first tubing section 36 into the third tubing section 46 is sealed by means of the silicone adhesive 40. Thus, fluids injected into the injection site 14 flow along a common axis to the bag inlet 24 along separate fluid pathways depending upon which injection port the fluids were injected into.

Four medicinal tubes 34 are substantially equidistantly spaced about a portion of the exterior surface 26 of the flexible bag 12. Each medicinal tube 34 includes a first open end 56 which is placed in open fluid communication with fluid injected into the second self-sealing dome 22 and carried by the third section of surgical tubing 46. In this regard, the first open ends 56 of the medicinal tubes 34 extend slightly through the wall of the third section of surgical tubing 46 at a point adjacent to the bag inlet 24. The first open ends 56 are secured in place by means of the silicone adhesive 40 such that open fluid communication is ensured between the fluid passageway defined by the annular space within the third section of tubing 46 which surrounds the first section of tubing 36. The medicinal tubes 34 each include a plurality of apertures 58 through which medication may escape into the cavity void between the cavity walls and the exterior surface 26 of the flexible bag 12. The second ends 60 of the medicinal tubes 34 are plugged or closed in order to help ensure that medication escaping through the apertures 58 is somewhat uniformly dispersed about the flexible bag 12 within the cavity.

Figure 5:
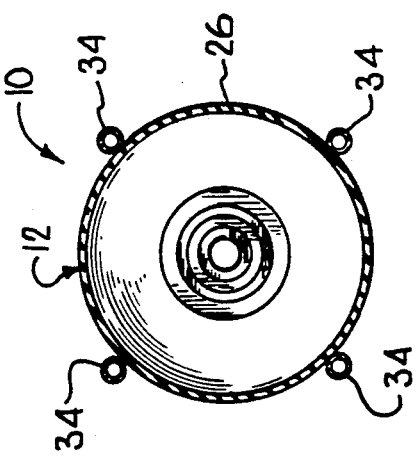
FIG. 5 is a fragmented sectional view taken generally along the line 5—5 of FIG. 1.
Figure 4:
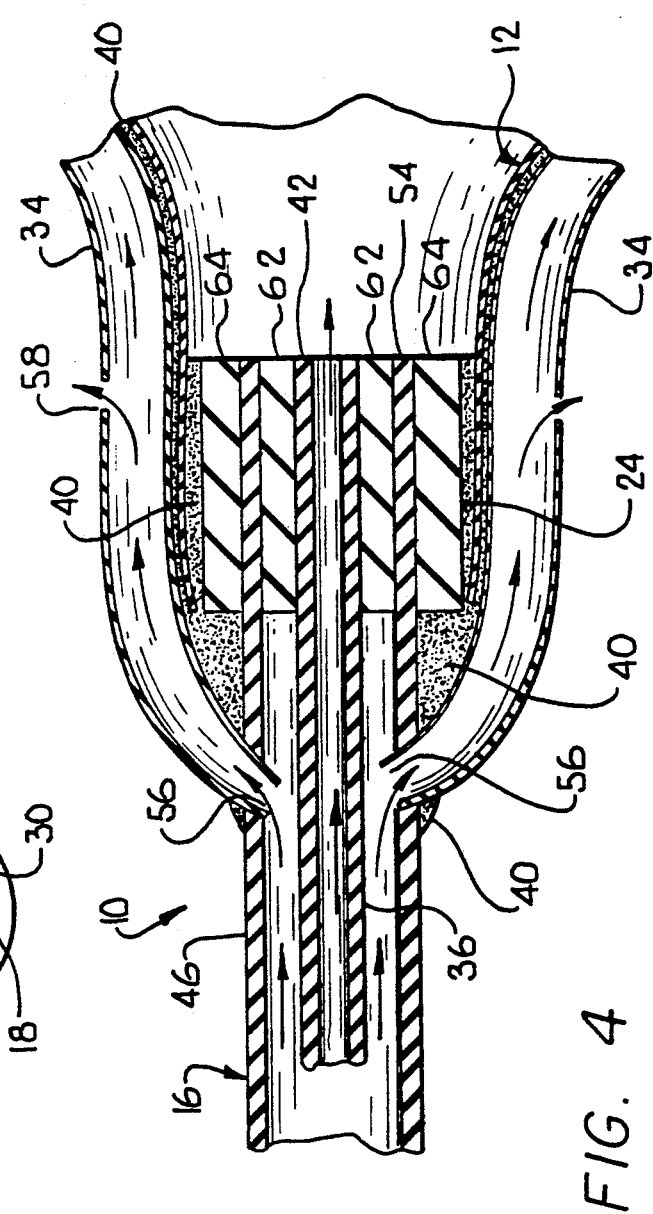
FIG. 4 is an enlarged fragmented sectional view of the area indicated by the line 4 in FIG. 3, illustrating the construction of the tumor access device in the region surrounding the outlet to the fluid conduits and an inlet for the fluid impermeable bag.

As illustrated best in FIGS. 4 and 5, a fourth short segment of tubing 62 is placed about the second open end 42 of the first section of tubing 36 and provides a plug for the annular space between the first section of tubing and the terminal end 54 of the third section of tubing 46. A fifth short segment of tubing 64 surrounds the terminal end 54 of the third section of tubing 46 to provide a plug to which the inlet 24 of the flexible bag 12 is attached. In this regard, the bag inlet 24 is secured to the exterior surface of the fifth segment of tubing 64 by means of the silicone adhesive 40, which adhesive is utilized also to adhere the medicinal tubes 34 to the exterior surface 26 of the flexible bag 12.

In order to facilitate x-ray detection of the positioning and configuration of the tumor access device 10 when subcutaneously implanted, it is preferred that the sections of tubing be barium impregnated, and that radiopaque encircling markers 66 be provided on the exterior surface 26 of the flexible bag 12. These radiopaque markers are preferably of a tantalum material covered with a silicone coating to ensure that the entire device 10 presents only exposed surfaces of materials having known and acceptable tissue reaction properties.

The tumor access device 10 thus described facilitates a novel treatment method for accessing a body cavity through a relatively small cavity wall aperture, and for delivering medication into the body cavity. For example, in the treatment of cancer where a tumor has been completely or partially removed to leave a body cavity, following the excision a relatively small cavity wall aperture would be provided. The fluid impermeable bag 12 is inserted into the body cavity through the cavity wall aperture, and then the injection site 14 is implanted at a location remote from the body cavity. The fluid conduit 16 is also subcutaneously implanted to provide the link between the injection site and the flexible bag.

A sterile fluid, preferably a sterile saline solution, is injected through the first self-sealing dome 20 in a quantity sufficient to inflate the bag 12 to substantially fill the body cavity. This process also tends to block off the cavity wall aperture so that fluids injected into the space between the cavity walls and the exterior surface 26 of the flexible bag 12 are held therein. The bag 12 may be either non-distensible to limit the ultimate size and shape of the inflated bag, or distensible to accommodate varied body cavity geometries.

Once the flexible bag 12 has been inflated to the desired size (which can be detected through x-ray photography), medication is then injected through the second self-sealing dome 22 into the medication injection chamber which is open fluid communication with the medicinal tubes 34. Accordingly, fluid injected through the second self-sealing dome 22 flows through the annular space defined by the third section of surgical tubing 46 and the first section of surgical tubing 36 into the medicinal tubes 34 which are positioned within the body cavity, and is allowed to escape through the apertures 58 provided therethrough.

The tumor access device 10 of the present invention further lends itself to simplified removal from the body cavity upon completion of the prescribed treatment. In particular, a needle can be injected through the first self-sealing dome 20 for purposes of withdrawing the saline solution from within the flexible bag 12 until the bag has been deflated within the body cavity. After the bag has been deflated, it is a simple process to remove the bag 12 from the body cavity by pulling it through the cavity wall aperture as the tumor access device 10 is removed from the patient. This eliminates the requirement to resect the walls of the body cavity.

From the foregoing it is to be appreciated that the novel tumor access device 10 provides an article which is of simplified construction, is entirely subcutaneously implantable and accessible by injection, and further provides a novel method of delivering medication into a body cavity. The flexible bag substantially fills the void within the cavity, thus requiring that a minimum of medication be utilized in the treatment of the tissue defining the cavity walls.

Although a particular embodiment of the invention has been described in detail for purposes of illustration, various modifications may be made without departing from the spirit and scope of the invention. Accordingly, the invention is not to be limited, except as by the appended claims.

We claim:

1. A surgically implantable device for accessing a body cavity through a relatively small cavity wall aperture, and delivering medication through the device into the body cavity, the device comprising:
   means for receiving a first fluid subcutaneously by injection into the device at a location remote from the body cavity;
   a first conduit extending from the first fluid receiving means to the cavity wall aperture;
   a flexible, fluid impermeable bag configured for insertion into the body cavity through the cavity wall aperture, the fluid impermeable bag having an exterior surface and a bag inlet connected to the first conduit opposite to the first fluid receiving means such that fluid injected into the first fluid receiving means flows into the fluid impermeable bag to inflate it within the body cavity, and such that fluid withdrawn from the first fluid receiving means collapses the fluid impermeable bag permitting it to be withdrawn from the body cavity;
   means for receiving by injection, at a location remote from the fluid impermeable bag, medication into the device;
   a second conduit connected to the medication receiving means and extending adjacent to the first conduit to the cavity wall aperture; and
   means for delivering the medication from the medication receiving means into a space between walls defining the body cavity and the exterior surface of the fluid impermeable bag, wherein the medication delivering means includes at least one medication outlet which directs the medication injected into the medication receiving means into said space such that the medication substantially surrounds the fluid impermeable bag.

2. A device as set forth in claim 1, wherein the fluid impermeable bag includes encircling radiopaque markers.

3. A device as set forth in claim 1, wherein the second conduit is coaxial with and surrounds at least a portion of the first conduit.

4. A device as set forth in claim 12, wherein the medication delivering means includes a plurality of medicinal tubes, each having a first end in fluid communication with the second conduit, wherein the medicinal tubes are attached to and extend substantially equidistantly about a portion of the exterior surface of the fluid impermeable bag, each of said medicinal tubes including a plurality of medication outlets.

5. A device as set forth in claim 1, wherein the first fluid receiving means includes a first injection port comprising a first base and a first self-sealing dome which define therebetween a fluid injection chamber, and wherein the medication receiving means includes a second injection port comprising a second base and a second self-sealing dome which define therebetween a medication injection chamber, and wherein the first and second injection ports are co-located and share a common base, wherein a needle guard is positioned within each of the injection chambers adjacent to the base.

6. A surgically implantable device for accessing a body cavity through a relatively small cavity wall aperture, and delivering medication through the device into the body cavity, the device comprising:
   a flexible, fluid impermeable bag configured for insertion into the body cavity through the cavity wall aperture, the fluid impermeable bag having a bag inlet and an exterior surface;
   means for receiving by injection, at a location remote from the fluid impermeable bag, a fluid utilized for inflating the fluid impermeable bag;
   a fluid conduit connecting the fluid impermeable bag to the inflating fluid receiving means, such that fluid injected into the inflating fluid receiving means passes through the fluid conduit and the bag inlet to inflate the fluid impermeable bag;
   means for receiving by injection, at a location remote from the fluid impermeable bag, medication into the device; and
   means for delivering the medication from the medication receiving means into a space between the walls of the body cavity and the exterior surface of the fluid impermeable bag;
   wherein the inflating fluid receiving means includes a first injection port comprising the first base and a first self-sealing dome which define therebetween a fluid injection chamber, wherein a first open end of the fluid conduit is attached to the first injection port such that fluid injected into the fluid injection chamber freely passes through the first open end of the fluid conduit for delivery to the fluid impermeable bag.

7. A device as set forth in claim 6, wherein the medication receiving means includes a second injection port comprising a second base and a second self-sealing dome which define therebetween a medication injection chamber, wherein a second open end of the fluid conduit is attached to the second injection port such that fluid injected into the medication injection chamber freely passes through the second open end of the fluid conduit for delivery to the medication delivering means.

8. A device as set forth in claim 7, wherein the first and second injection ports are co-located and share a common base, and wherein a needle guard is positioned within each of the injection chambers adjacent to the base.

9. A surgically implantable device for accessing a body cavity through a relatively small cavity wall aperture, and delivering medication through the device into the body cavity, the device comprising:
   a flexible, fluid impermeable bag configured for insertion into the body cavity through the cavity wall aperture, the fluid impermeable bag having a bag inlet and an exterior surface;

means for receiving by injection, at a location remote from the fluid impermeable bag, a fluid utilized for inflating the fluid impermeable bag;

a fluid conduit connecting the fluid impermeable bag to the inflating fluid receiving means, such that fluid injected into the inflating fluid receiving means passes through the fluid conduit and the bag inlet to inflate the fluid impermeable bag;

means for receiving by injection, at a location remote from the fluid impermeable bag, medication into the device; and means for delivering the medication from the medication receiving means into a space between the walls of the body cavity and the exterior surface of the fluid impermeable bag;

wherein the fluid conduit extends between and connects the medication receiving means and the medication delivering means, such that fluid injected into the medication receiving means passes through the fluid conduit into the medication delivering means for passage into the space between the walls of the body cavity and the exterior surface of the fluid impermeable bag, and wherein the fluid conduit includes a first section of tubing having a first end which receives fluid injected into the inflating fluid receiving means, and a second end which discharges fluid passing therethrough into the fluid impermeable bag through the bag inlet, the fluid conduit further including a second section of tubing which is coaxial with and surrounds the first section of tubing for at least a portion of the length of the fluid conduit, and which has a first end which receives fluid injected into the medication receiving means, and a second end which discharges fluid into the medication delivering means.

10. A device as set forth in claim 9, wherein the fluid impermeable bag includes radiopaque markers.

11. A device as set forth in claim 9, wherein the fluid impermeable bag is distensible to accommodate varied body cavity geometries.

12. A device as set forth in claim 9, wherein the medication delivering means includes at least one medicinal tube having an end in fluid communication with medication injected into the medication receiving means, wherein the medicinal tube is attached to and extends about a portion of the exterior surface of the fluid impermeable bag, and includes at least one aperture through which medication is delivered into the space between the walls of the body cavity and the exterior surface of the fluid impermeable bag.

13. A device as set forth in claim 12, wherein the medication delivering means includes a plurality of medicinal tubes each having a first end in fluid communication with medication injected into the medication receiving means, and a second plugged end, wherein the medicinal tubes are attached to and extend substantially equidistantly about a portion of the exterior surface of the fluid impermeable bag, and each includes at least one aperture through which medication is delivered into the space between the walls of the body cavity and the exterior surface of the fluid impermeable bag.

14. A device as set forth in claim 9, wherein the inflating fluid receiving means includes a first injection port comprising a firs base and a first self-sealing dome which define therebetween a fluid injection chamber, wherein a first open end of the fluid conduit is attached to the first injection port such that fluid injected to the fluid injection chamber freely passes through the first open end of the fluid conduit for delivery to the fluid impermeable bag.

15. A device as set forth in claim 14, wherein the medication receiving means includes a second injection port comprising a second base and a second self-sealing dome which define therebetween a medication injection chamber, wherein a second open end of the fluid conduit is attached to the second injection port such that fluid injected into the medication injection chamber freely passes through the second open end of the fluid conduit for delivery to the medication delivering means.

16. A device as set forth in claim 15, wherein the first and second injection ports are co-located and share a common base, and wherein a needle guard is positioned within each of the injection chambers adjacent to the base.

17. A method for delivering a medication into a body cavity, the steps comprising:

inflating a flexible bag within the body cavity utilizing a sterile fluid, such that the flexible bag expands a fill most of the void of the body cavity; and injecting medication into the space between an exterior surface of the flexible bag and the cavity wall such that the medication substantially surrounds the flexible bag and fills the remaining void;

wherein the steps of inflating the flexible bag and injecting medication are accomplished through subcutaneous injection at a site remote from the body cavity.

18. A method as set forth in claim 17, including the step of inserting the flexible bag into the body cavity through a cavity wall aperture, wherein the fluid impermeable bag includes a bag inlet and an exterior surface, and the step of implanting a fluid conduit which connects the fluid impermeable bag to the injection site such that fluid injected into the injection site passes through the fluid conduit to the bag inlet for inflating the flexible bag within the body cavity.

19. A method as set forth in claim 18, wherein the injection site comprises means for receiving by injection the sterile fluid utilized to inflate the fluid impermeable bag, and means for receiving by injection a medication into the device, wherein the medication receiving means is separable from the inflating fluid receiving means.

20. A method as set forth in claim 19, wherein the fluid conduit includes a first section of tubing having a first end which receives fluid injected into the inflating fluid receiving means, and a second end which discharges fluid passing therethrough into the fluid impermeable bag such that fluid injected into the inflating fluid receiving means inflates the flexible bag within the body cavity.

21. A method as set forth in claim 20, wherein the fluid conduit includes a second section of tubing having a first end which receives fluid injected into the medication receiving means, and a second end which discharges fluid in a manner permitting delivery thereof into the space between the exterior surface of the flexible bag and the cavity wall.

22. A method as set forth in claim 21, wherein the second section of tubing is coaxial with and surrounds the first section of tubing for at least a portion of the length of the fluid conduit.

23. A method as set forth in claim 19, wherein the inflating fluid receiving means includes a first base and a first self-sealing dome which define therebetween a fluid injection chamber, wherein the medication receiving means comprises a second base and a second self-sealing dome which define therebetween a medication injection chamber, and wherein the inflating fluid receiving means and the medication receiving means are co-located such that the first and second bases form a unitary base structure.

24. A method as set forth in claim 18, wherein the step of injecting medication utilizes means for delivering the medication into the space between the exterior surface of the flexible bag and the cavity wall, wherein the medication delivering means includes at least one medicinal tube having an end in fluid communication with the fluid conduit, wherein the medicinal tube is attached to and extends about a portion of the exterior surface of the fluid impermeable bag and includes a plurality of apertures through which medication is delivered into the space between the walls of the body cavity and the exterior surface of the fluid impermeable bag.

25. A method as set forth in claim 24, wherein the medication delivering means includes a plurality of medicinal tubes, each having a first end in fluid communication with medication injected at the injection site, and a second plugged end, wherein the medicinal tubes are attached to and extend substantially equidistantly about a portion of the exterior surface of the fluid impermeable bag.

26. A method for accessing a body cavity through a relatively small cavity wall aperture, and for delivering medication into the body cavity, the steps comprising:
  inserting a flexible, fluid impermeable bag into the body cavity through the cavity wall aperture;
  implanting an injection site at a location remote from the body cavity, and a fluid conduit extending between the injection site and a bag inlet;
  injecting fluid into the injection site in a manner and in quantities sufficient to inflate the bag to substantially fill the body cavity; and
  injecting medication into the injection site such that the medication is directed into the body cavity between the flexible bag and the walls of the body cavity.

27. A method as set forth in claim 26, wherein the fluid conduit includes a first conduit extending from the injection site to the cavity wall aperture, and a second conduit connected to the injection site and coaxially extending with the first conduit to the cavity wall aperture.

28. A method as set forth in claim 27, wherein the step of injecting medication such that the medication is directed into the body cavity between the flexible bag and the walls of the body cavity, is effected by means for delivering the medication from the injection site through the second conduit into a space between the walls defining the body cavity and the exterior surface of the fluid impermeable bag, wherein the medication delivering means includes a plurality of medication outlets which direct the medication injected into the injection site into said space such that the medication substantially surrounds the fluid impermeable bag.

29. A method as set forth in claim 28, wherein the medication delivering means includes at least one medicinal tube having an end in fluid communication with the second fluid conduit, wherein the medicinal tube is attached to and extends about a portion of the exterior surface of the fluid impermeable bag, and includes a plurality of apertures through which medication is delivered into the space between the walls of the body cavity and the exterior surface of the fluid impermeable bag.

30. A method as set forth in claim 27, wherein the injection site includes means for receiving a first fluid subcutaneously by injection into the device at a location remote from the body cavity, the inflating fluid receiving means including a first base and a first self-sealing dome which define therebetween a fluid injection chamber, wherein a first open end of the first conduit is attached to the inflating fluid receiving means such that fluid injected into the fluid injection chamber freely passes through the first open end of the first conduit for delivery to the bag inlet.

31. A method as set forth in claim 30, wherein the injection site further includes means for receiving by injection, at a location remote from the fluid impermeable bag, medication into the device, the medication receiving means including a second base and a second self-sealing dome which define therebetween a medication injection chamber, wherein the first end of the second conduit is attached to the medication receiving means such that fluid injected into the medication injection chamber freely passes through the second conduit, wherein the inflating fluid receiving means and the medication receiving means, although defining separate fluid reception sites, are co-located such that the first and second bases form a unitary base structure, and wherein a needle guard is positioned within each of the injection chambers adjacent to the base.

32. A method as set forth in claim 26, including the step of detecting the configuration of the fluid impermeable bag within the body cavity by means of x-ray detection, wherein for this purpose the fluid impermeable bag includes radiopaque markers.

33. A method as set forth in claim 26, wherein the fluid-impermeable bag is distensible so as to conform to varied body cavity geometries as the bag is inflated.

* * * * *

UNITED STATES PATENT AND TRADEMARK OFFICE
CERTIFICATE OF CORRECTION

PATENT NO. : 5,112,303
DATED : May 12, 1992
INVENTOR(S) : Robert H. Pudenz and Gary P. East It is certified that error appears in the above-identified patent and that said Letters Patent is hereby corrected as shown below:

In column 7, line 63, delete "12" and insert therefor --1--.

In column 8, line 38, delete "the" and insert therefor --a--.

In column 9, line 64, delete "firs" and insert therefor --first--.

In column 9, line 67, delete "to" (2nd occurrence) and insert therefore --into--.

Signed and Sealed this

Sixth Day of July, 1993

Attest:

MICHAEL K. KIRK

*Attesting Officer*   Acting Commissioner of Patents and Trademarks